(12) United States Patent
Kehres et al.

(10) Patent No.: US 11,553,930 B2
(45) Date of Patent: Jan. 17, 2023

(54) GLENOID REAMER

(71) Applicant: Biomet Manufacturing, LLC, Warsaw, IN (US)

(72) Inventors: Clinton E. Kehres, Warsaw, IN (US); Nathan A. Winslow, Warsaw, IN (US); Daniel D. Fritzinger, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 544 days.

(21) Appl. No.: 16/447,184

(22) Filed: Jun. 20, 2019

(65) Prior Publication Data

US 2019/0298393 A1 Oct. 3, 2019

Related U.S. Application Data

(60) Continuation of application No. 15/227,193, filed on Aug. 3, 2016, now Pat. No. 10,363,047, which is a division of application No. 13/324,188, filed on Dec. 13, 2011, now Pat. No. 9,408,613.

(51) Int. Cl.
*A61B 17/16* (2006.01)

(52) U.S. Cl.
CPC ...... *A61B 17/1617* (2013.01); *A61B 17/1631* (2013.01); *A61B 17/1642* (2013.01); *A61B 17/1659* (2013.01); *A61B 17/1684* (2013.01)

(58) Field of Classification Search
CPC . A61B 17/16; A61B 17/1615; A61B 17/1617; A61B 17/1631; A61B 17/1642; A61B 17/1657; A61B 17/1659; A61B 17/1684; A61F 2/40; A61F 2/4081

See application file for complete search history.

(56) References Cited

U.S. PATENT DOCUMENTS

| | | | |
|---|---|---|---|
| 5,489,310 A | * | 2/1996 | Mikhail ............ A61B 17/1684 623/19.11 |
| 7,608,076 B2 | | 10/2009 | Ezzedine |
| 8,366,713 B2 | | 2/2013 | Long et al. |
| 9,408,613 B2 | | 8/2016 | Kehres et al. |

(Continued)

OTHER PUBLICATIONS

"U.S. Appl. No. 13/324,188, Advisory Action dated Nov. 10, 2014", 3 pgs.

(Continued)

*Primary Examiner* — Si Ming Ku
(74) *Attorney, Agent, or Firm* — Schwegman Lundberg & Woessner, P.A.

(57) ABSTRACT

A bone reamer includes a first member having a first hub and a second member having a second hub. The first hub can extend along a first axis and have a pair of elongated cutting arms that are fixed to the first hub. The elongated cutting arms can extend along a second axis that is generally perpendicular relative to the first axis. The first hub can define a track thereon. The second hub can extend along a third axis. The second member can have a second pair of elongated cutting arms that are fixed to the second hub and extend along a fourth axis that is generally perpendicular to the third axis. The second member can have a track follower extending thereon and that is configured to slidably advance along the track causing the first and second members to move between a collapsed position and an expanded position.

16 Claims, 9 Drawing Sheets

(56) References Cited

U.S. PATENT DOCUMENTS

| | | | |
|---|---|---|---|
| 10,363,047 B2 | 7/2019 | Kehres et al. | |
| 2002/0095214 A1* | 7/2002 | Hyde, Jr. | A61F 2/4612 623/18.12 |
| 2004/0167528 A1* | 8/2004 | Schantz | A61B 17/1666 606/81 |
| 2006/0217730 A1 | 9/2006 | Termanini | |
| 2007/0038302 A1 | 2/2007 | Shultz et al. | |
| 2008/0009874 A1 | 1/2008 | Meridew et al. | |
| 2011/0035007 A1 | 2/2011 | Patel et al. | |
| 2011/0213371 A1 | 9/2011 | Anthony et al. | |
| 2012/0239042 A1* | 9/2012 | Lappin | A61B 17/1778 606/80 |
| 2013/0150859 A1 | 6/2013 | Kehres et al. | |
| 2017/0020535 A1 | 1/2017 | Kehres et al. | |

OTHER PUBLICATIONS

"U.S. Appl. No. 13/324,188, Final Office Action dated Sep. 4, 2014", 11 pgs.

"U.S. Appl. No. 13/324,188, Final Office Action dated Sep. 8, 2015", 12 pgs.

"U.S. Appl. No. 13/324,188, Non Final Office Action dated Jan. 26, 2015", 13 pgs.

"U.S. Appl. No. 13/324,188, Non Final Office Action dated Apr. 29, 2014", 11 pgs.

"U.S. Appl. No. 13/324,188, Notice of Allowance dated Apr. 8, 2016", 9 pgs.

"U.S. Appl. No. 13/324,188, Response filed Dec. 8, 2015 to Final Office Action dated Sep. 8, 2015", 12 pgs.

"U.S. Appl. No. 13/324,188, Restriction Requirement dated Apr. 4, 2014", 6 pgs.

"U.S. Appl. No. 15/227,193, Examiner interview Summary dated Apr. 11, 2017", 3 pgs.

"U.S. Appl. No. 15/227,193, Examiner Interview Summary dated Aug. 18, 2017", 3 pgs.

"U.S. Appl. No. 15/227,193, Examiner interview Summary dated Aug. 27, 2018", 3 pgs.

"U.S. Appl. No. 15/227,193, Final Office Action dated Jun. 26, 2018", 12 pgs.

"U.S. Appl. No. 15/227,193, Final Office Action dated Jun. 27, 2017", 11 pgs.

"U.S. Appl. No. 15/227,193, Non Final Office Action dated Feb. 10, 2017", 10 pgs.

"U.S. Appl. No. 15/227,193, Non Final Office Action dated Nov. 3, 2017", 15 pgs.

"U.S. Appl. No. 15/227,193, Notice of Allowance dated Mar. 20, 2019", 11 pgs.

"U.S. Appl. No. 15/227,193, Preliminary Amendment filed Oct. 10, 2016", 6 pgs.

"U.S. Appl. No. 15/227,193, Response filed Jan. 6, 2017 to Restriction Requirement dated Dec. 9, 2016", 7 pgs.

"U.S. Appl. No. 15/227,193, Response filed Feb. 9, 2018 to Non Final Office Action dated Nov. 3, 2017", 11 pgs.

"U.S. Appl. No. 15/227,193, Response filed May 10, 2017 to Non Final Office Aciton dated Feb. 10, 2017", 9 pgs.

"U.S. Appl. No. 15/227,193, Response filed Aug. 15, 2017 to Final Office Action dated Jun. 27, 2017", 10 pgs.

"U.S. Appl. No. 15/227,193, Response filed Dec. 26, 2018 to Final Office Action dated Jun. 26, 2018", 13 pgs.

"U.S. Appl. No. 15/227,193, Restriction Requirement dated Dec. 9, 2016", 8 pgs.

* cited by examiner

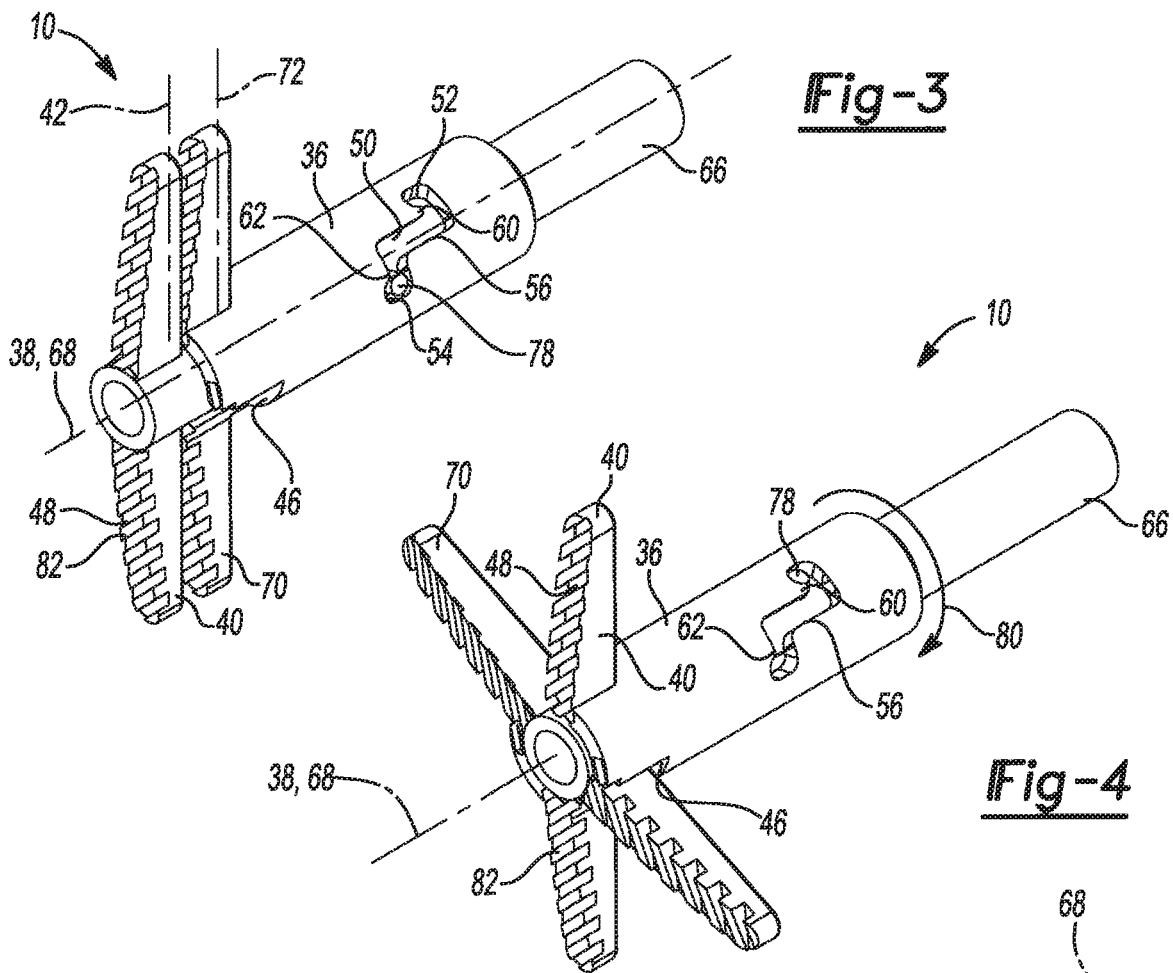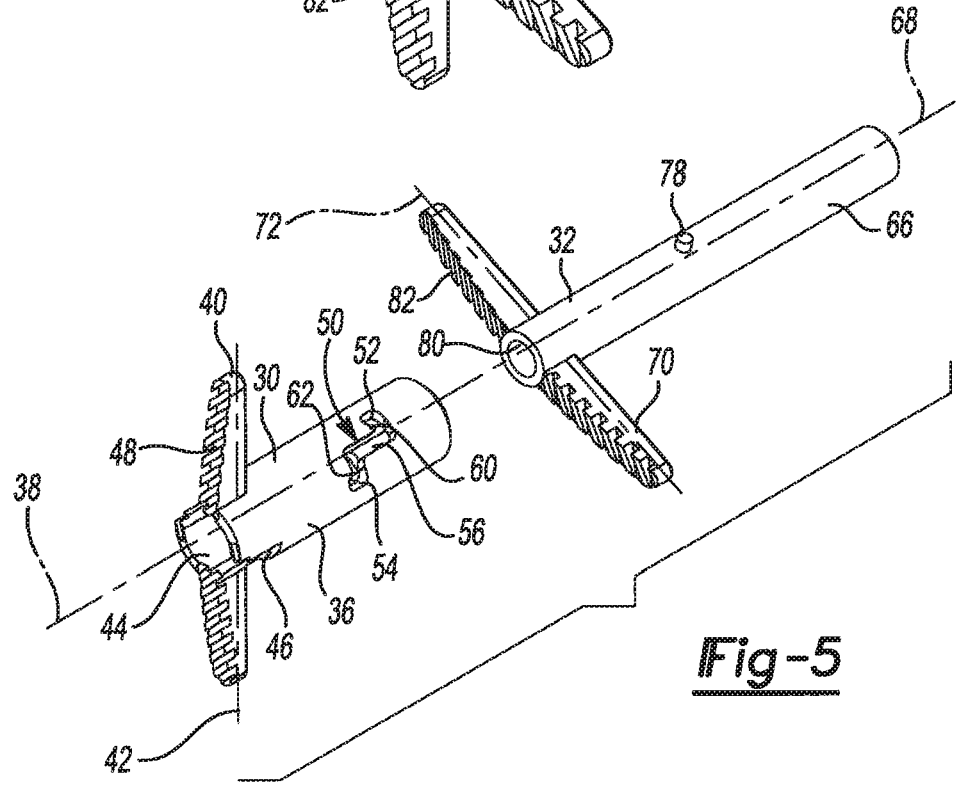

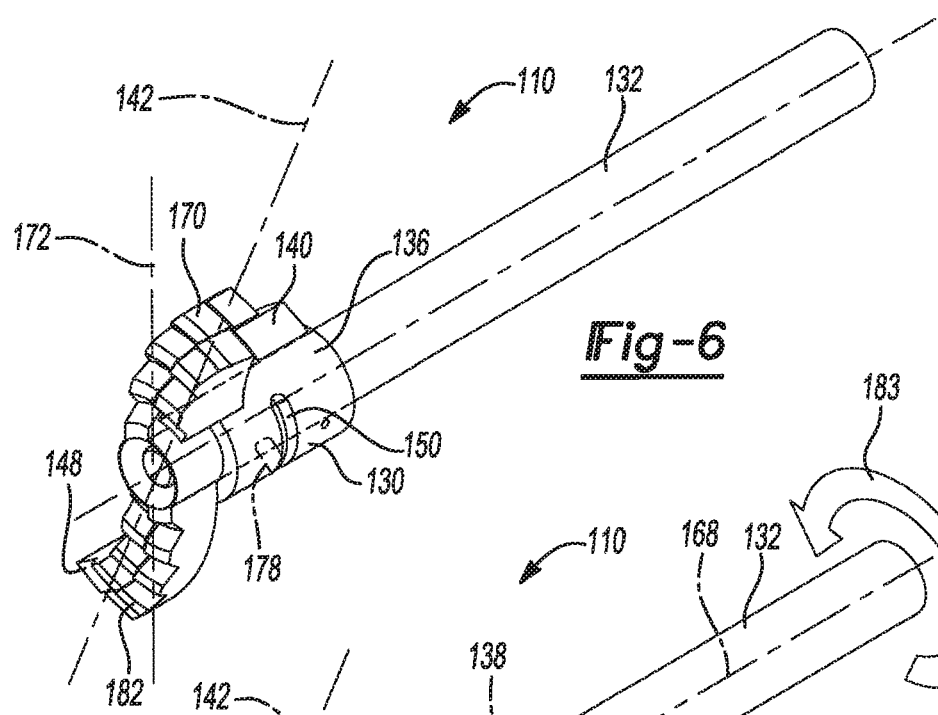
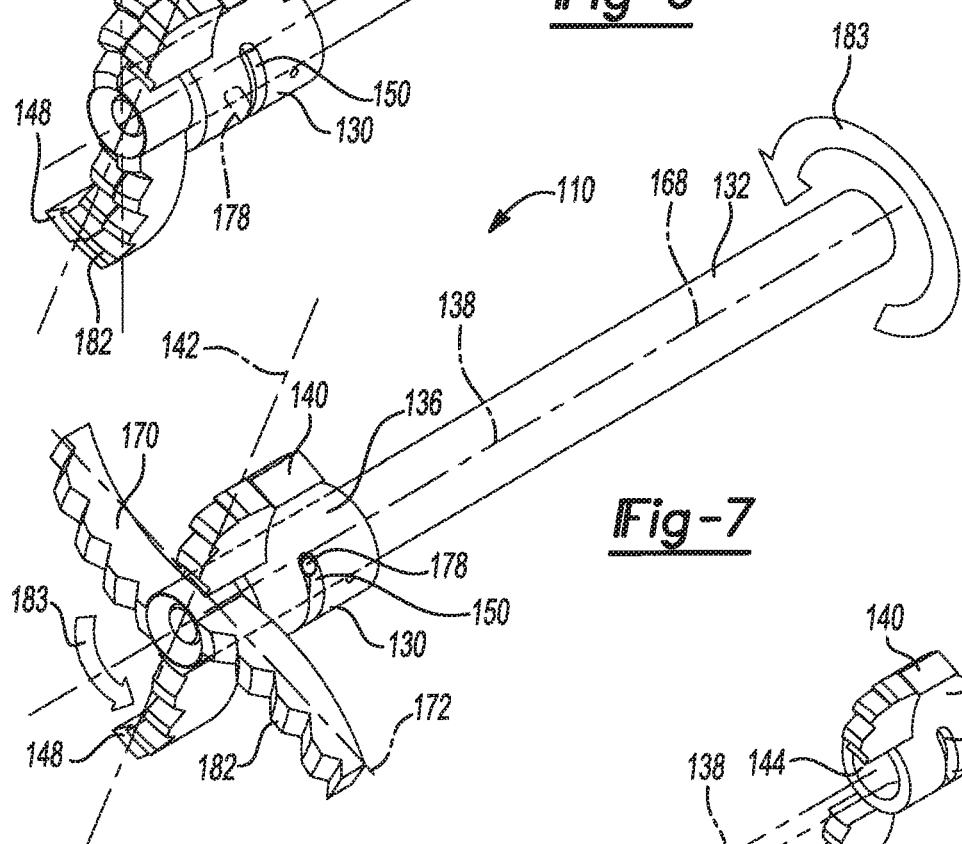
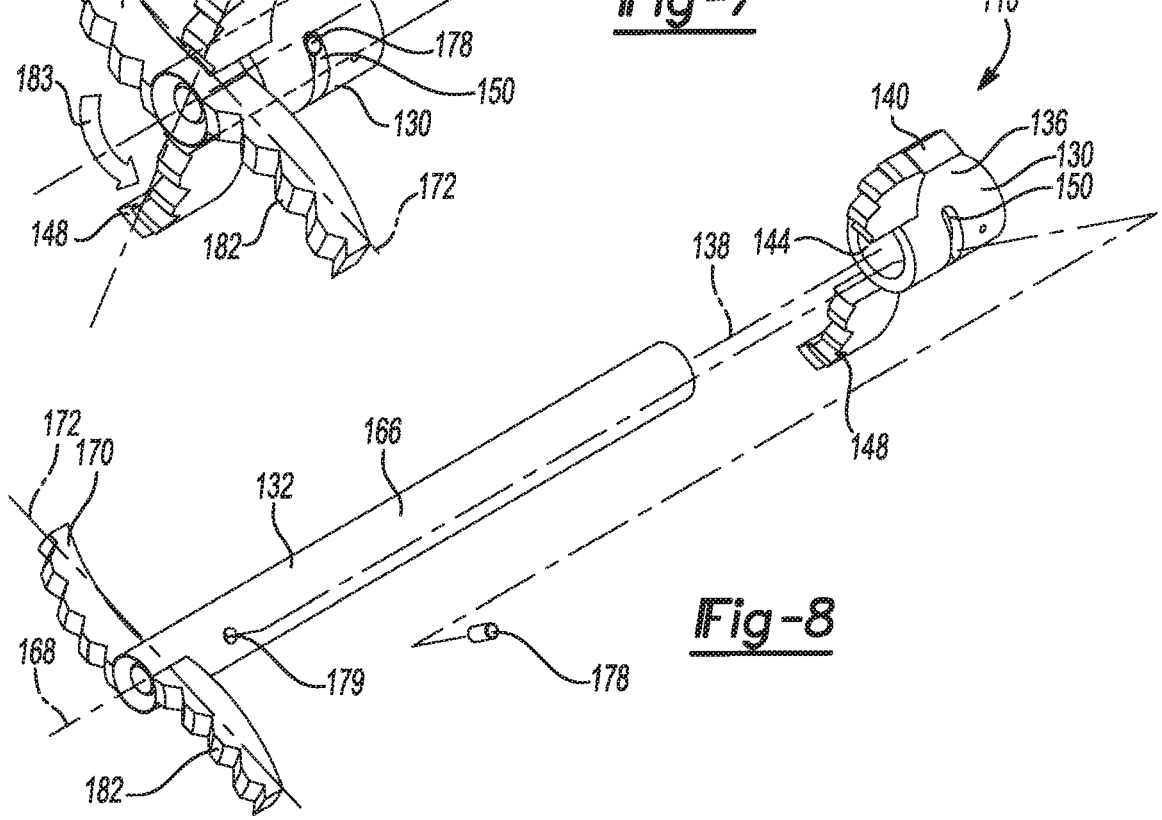

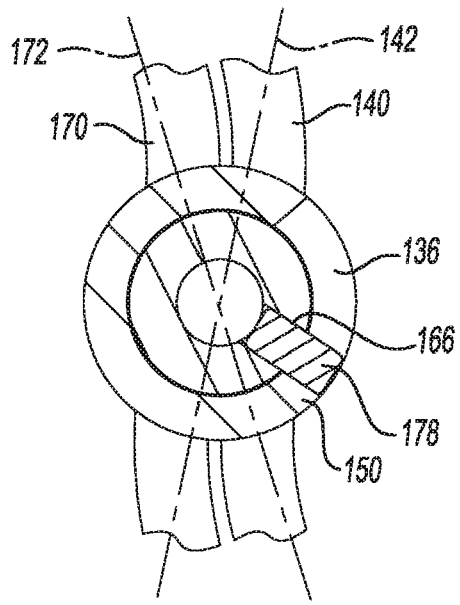
Fig-9
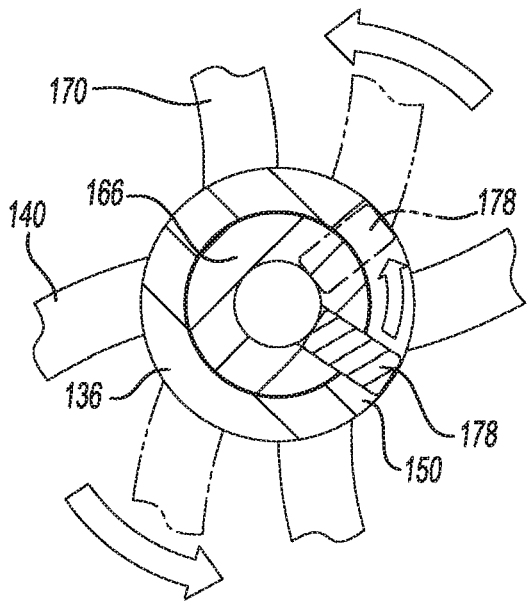
Fig-10
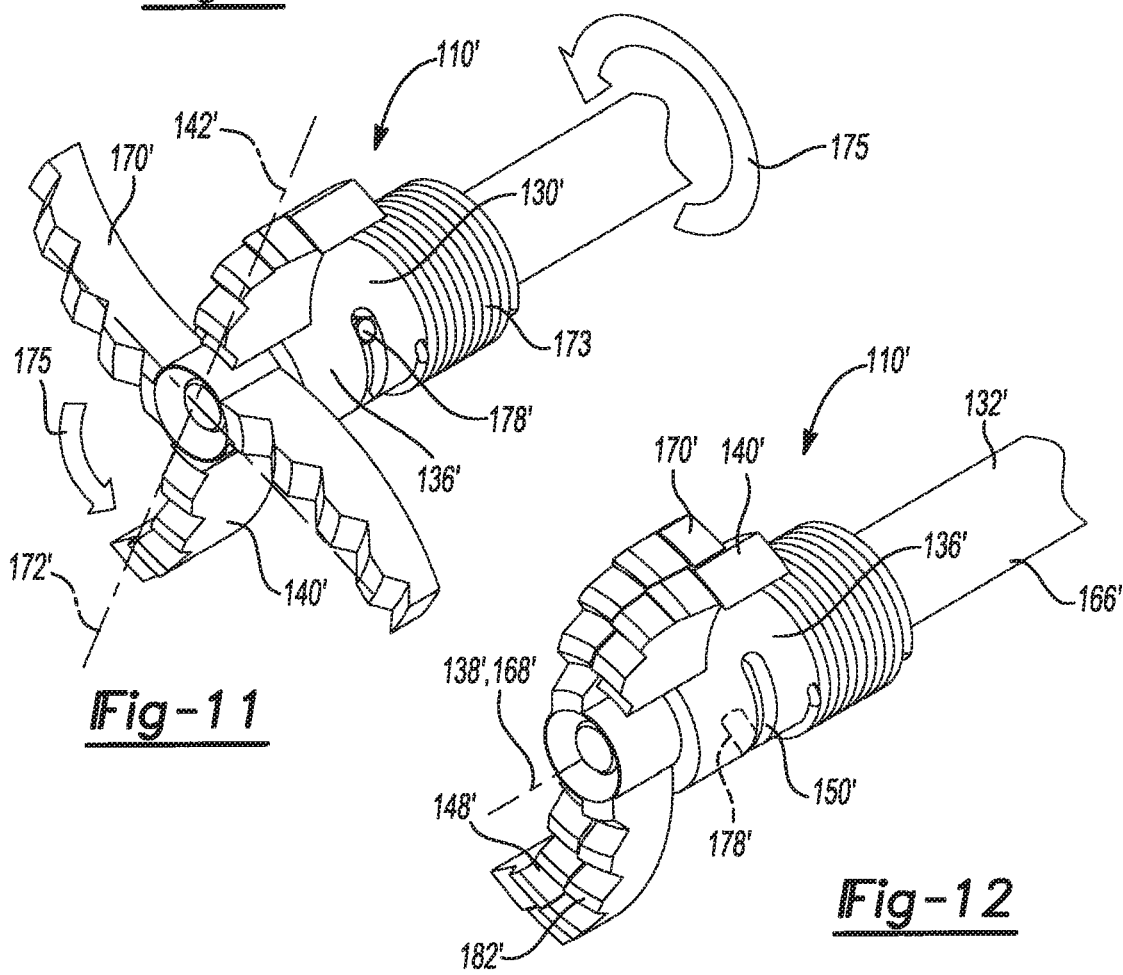
Fig-11
Fig-12

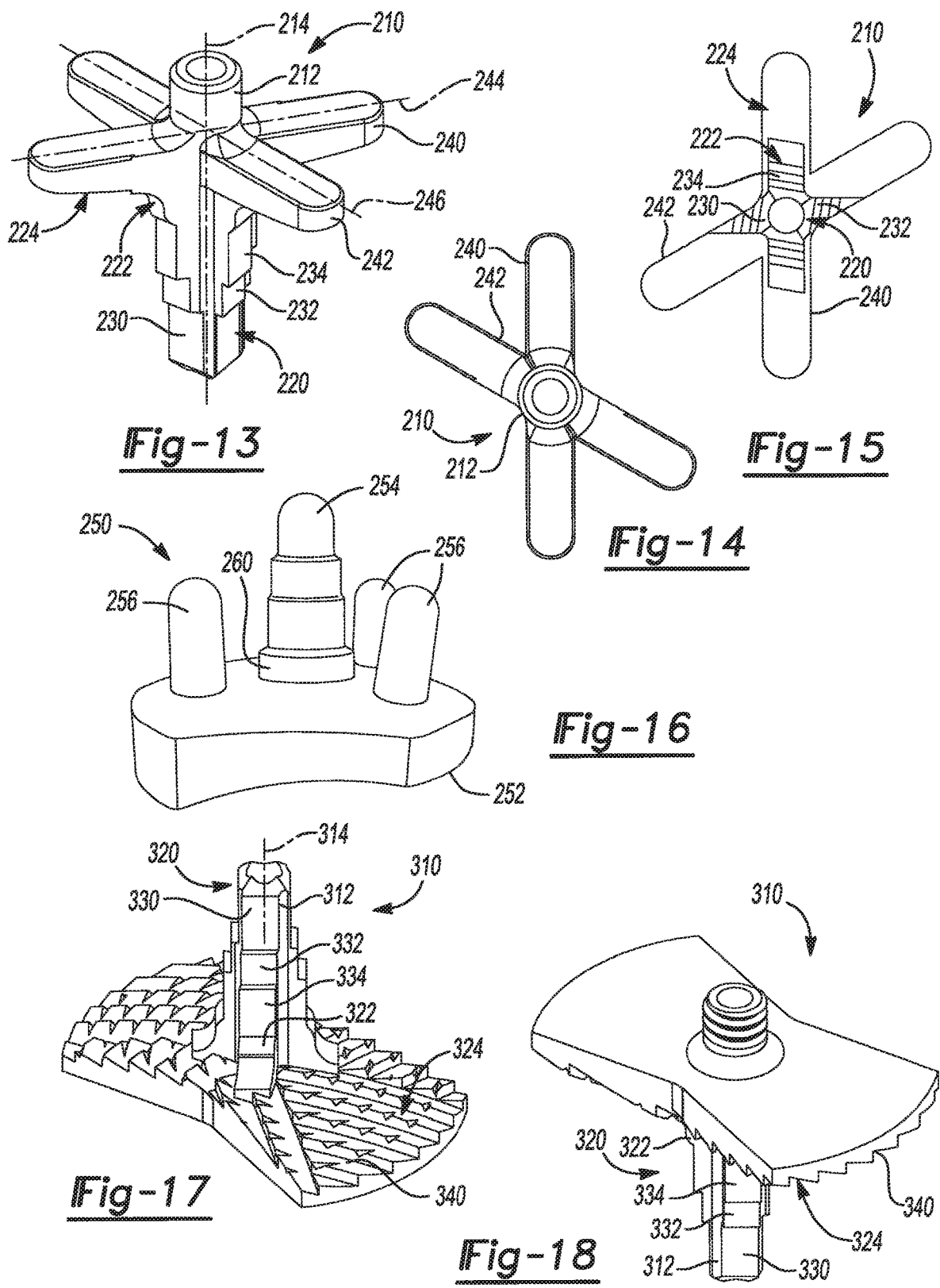

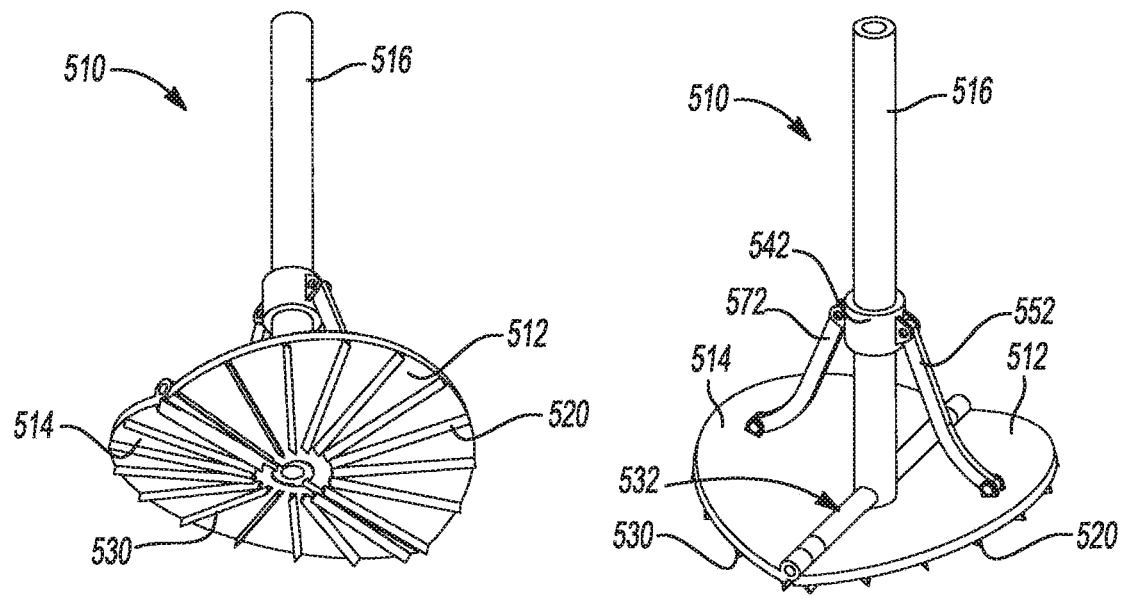
*Fig-25*
*Fig-26*
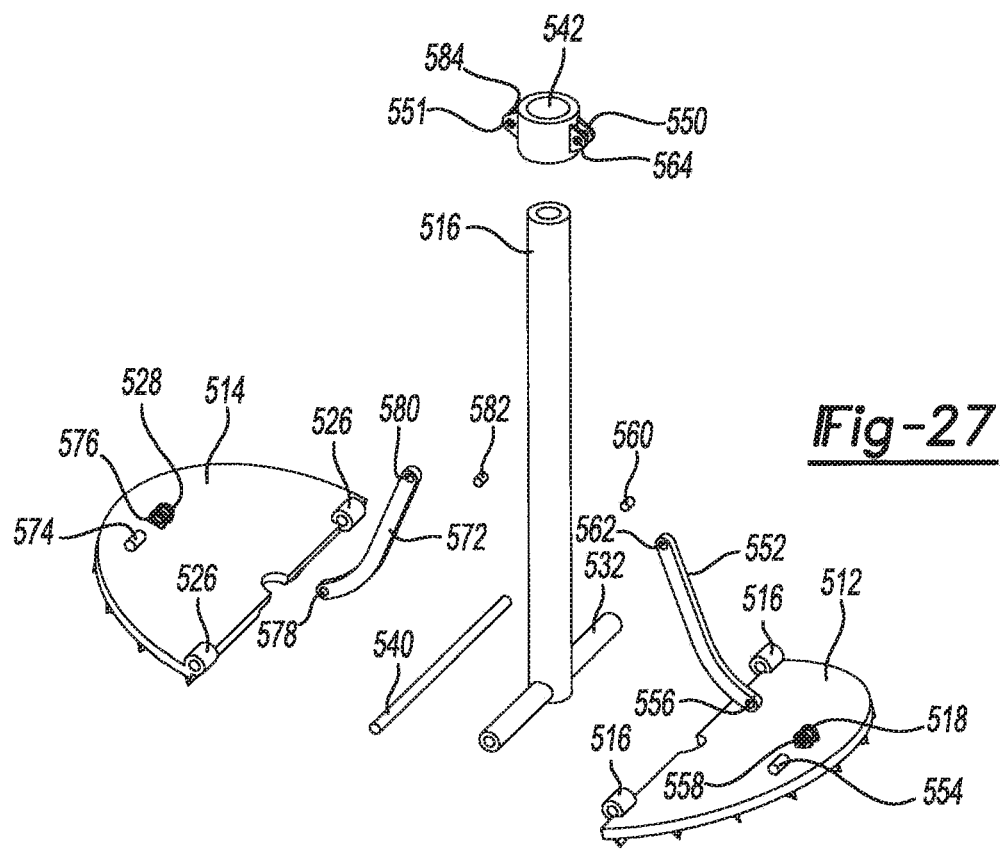
*Fig-27*

GLENOID REAMER

RELATED APPLICATION

This application is a continuation application of U.S. patent application Ser. No. 15/227,193, filed Aug. 3, 2016, which application is a Divisional Application of U.S. patent application Ser. No. 13/324,188, filed on Dec. 13, 2011, now U.S. Pat. No. 9,408,613 which issued on Aug. 9, 2016, the contents of which are hereby incorporated in their entireties.

FIELD

The present disclosure relates generally to a method for performing shoulder arthroplasty and, more particularly, to a glenoid reamer having a reduced profile for insertion through a small incision site.

BACKGROUND

This section provides background information related to the present disclosure which is not necessarily prior art.

A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of such a shoulder joint prosthesis becomes necessary, the natural head portion of the humerus may be resected and a cavity may be created in the intramedullary canal of the host humerus for accepting a humeral component. The humeral component may include a head portion used to replace the natural head of the humerus. Once the humeral component has been implanted, the glenoid cavity positioned at the glenoid may also be resurfaced and shaped to accept a glenoid component. The glenoid component generally includes an articulating surface which is engaged by the head portion of the humeral component.

During such shoulder arthroplasty, the glenoid may be difficult to access. In many instances, it may be necessary to create a large incision to allow the instruments, such as a reamer, required for the surgery to contact the glenoid and perform their intended use. Often, many surgeons prefer to make smaller incisions for a minimally invasive procedure because many benefits may be realized such as reduced bleeding, less post-operative pain, shorter recovery time, and smaller scars, Therefore, it is desirable to provide a glenoid reamer having a reduced profile suitable to be inserted through smaller incisions prepared in a patient's shoulder.

SUMMARY

This section provides a general summary of the disclosure, and is not a comprehensive disclosure of its full scope or all of its features.

A bone reamer constructed in accordance to one example of the present disclosure includes a first member having a first elongated hub and a second member having a second elongated hub. The first elongated hub can extend along a first axis and have a pair of elongated cutting arms that are fixed to the first elongated hub. The elongated cutting arms can extend along a second axis that is generally perpendicular relative to the first axis. The first elongated hub can define a track thereon. The second elongated hub can extend along a third axis. The second member can have a second pair of elongated cutting arms that are fixed to the second elongated hub and extend along a fourth axis that is generally perpendicular to the third axis. The second elongated hub can be concentrically mounted for rotatable movement with the first elongated hub. The second member can have a track follower extending thereon and that is configured to slidably advance along the track causing the first and second members to move between a collapsed position and an expanded position.

In the collapsed position, the first and second pair of cutting arms occupy a position where the second and fourth axes are substantially parallel. In the expanded position, the first and second pair of cutting arms occupy a position where the second and fourth axes are non-parallel.

According to additional features, the first and second elongated hubs can be cannulated. The second elongated hub can be received by the first elongated hub. The track can define a first track section, a second track section, and a third track section. The third track section can connect the first and second track sections. The third track section can be generally parallel to the first axis. The first and second tracks can define a first and a second hook, respectively. The first and second hooks can be configured to nestingly capture the track follower when the first and second members are in the expanded and collapsed positions, respectively.

In one configuration, the first member can occupy a position proximal relative to the second member in the collapsed position. The first elongated hub can define a relief thereon that is configured to receive the second pair of cutting arms in the expanded position. In another configuration, a biasing member can be disposed between the first and second members. The biasing member can be configured to bias the first and second members toward the collapsed position. Rotation of the reamer during a bone cutting event causes the second member to rotate relative to the first member from the collapsed position to the expanded position while overcoming the bias of the biasing member. The first and second pairs of cutting arms can have cutting teeth extending therefrom.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a front perspective view of the reamer shown in FIG. 1 and in the collapsed position;

FIG. 4 is a front perspective view of the reamer of FIG. 3 and shown in the expanded position;

FIG. 5 is an exploded front perspective view of the reamer of FIG. 3;

FIG. 6 is a front perspective view of a reamer constructed in accordance to additional features of the present disclosure and shown in a collapsed position;

FIG. 7 is a front perspective view of the reamer of FIG. 6 and shown in an expanded position;

FIG. 8 is an exploded front perspective view of the reamer of FIG. 6;

FIG. 9 is a distal end view of the reamer of FIG. 6 and shown in the collapsed position;

FIG. 10 is a distal end view of the reamer of FIG. 9 and shown with the arms being rotated during a reaming procedure;

FIG. 11 is a front perspective view of a reamer constructed in accordance to still another example of the present teachings and shown in an expanded position;

FIG. 12 is a front perspective view of the reamer of FIG. 11 and shown in a collapsed position;

FIG. 13 is a top perspective view of a glenoid reamer constructed in accordance to another example of the present teachings and including a glenoid face reamer; a boss cutter; and a modular post cutter formed as a single component;

FIG. 14 is a top plan view of the glenoid reamer shown in FIG. 13;

FIG. 15 is a bottom plan view of the glenoid reamer illustrated in FIG. 13;

FIG. 16 is a perspective view of an exemplary glenoid component;

FIG. 17 is a bottom perspective view of a glenoid reamer constructed in accordance to other features of the present disclosure;

FIG. 18 is a top perspective view of the glenoid reamer shown in FIG. 17;

FIG. 25 is a bottom perspective view of a glenoid reamer constructed in accordance to another example of the present teachings and shown in an expanded position;

FIG. 26 is a top perspective view of the glenoid reamer of FIG. 25;

FIG. 27 is an exploded perspective view of the glenoid reamer of FIG. 25;

Corresponding reference numerals indicate corresponding parts throughout the several views of the drawings.

DETAILED DESCRIPTION

Figure 1:
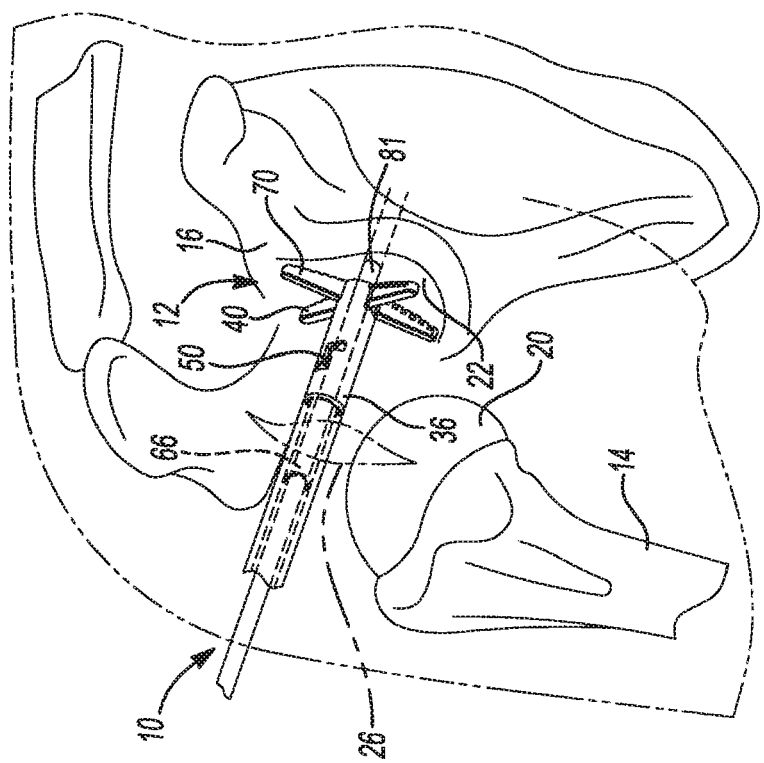
FIG. 1 is an anterior perspective view of a right glenohumeral joint and shown with a reamer constructed in accordance to one example of the present teachings in a collapsed position and inserted through an incision prepared in a patient.
Figure 2:
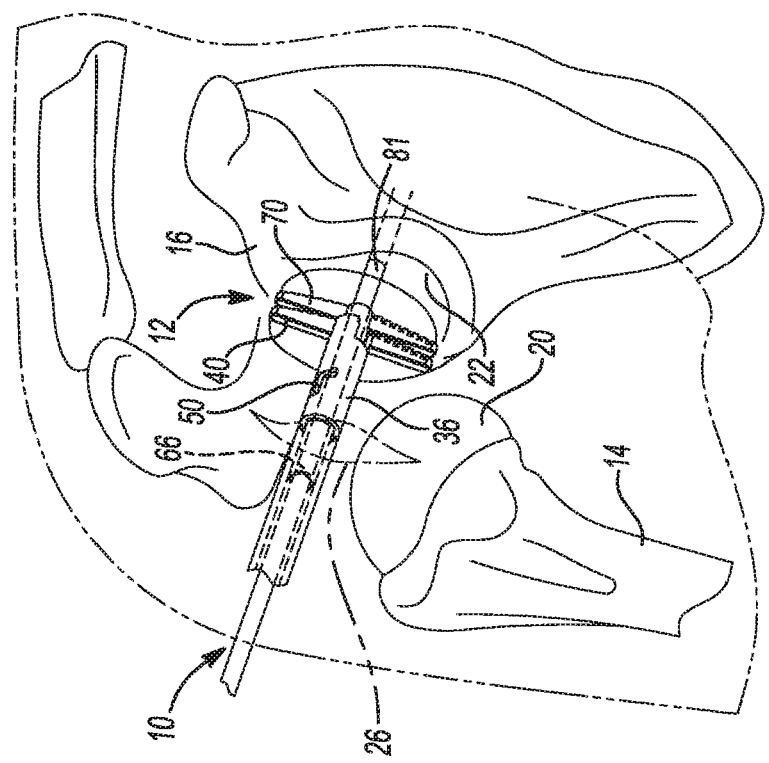
FIG. 2 is an anterior perspective view of the right glenohumeral joint shown in FIG. 1 and illustrated with the reamer in the expanded position for reaming the glenoid cavity.

Example embodiments will now be described more fully with reference to the accompanying drawings.

The following discussion will be directed generally toward various reamers constructed for use during shoulder arthroplasty. Those skilled in the art will be appreciate, however, that the reamers disclosed herein may also be used to prepare other portions of the body for receipt other prosthetic components such as, but not limited to, an acetabulum for receiving an acetabular cup. As used herein, the term "collapsed" is used to denote a position a reamer occupies that has a reduced footprint or profile on a distal end for passing through a small incision prepared in a patient. In the collapsed position, which may also be referred to as a "retracted" position, the reamer is in a configuration that takes up a reduced lateral space suitable for insertion or withdrawal through the incision in the patient. As used herein, the term "expanded" is used to denote a position a reamer occupies that has an increased profile on a distal end relative to the collapsed position. In the expanded position, which may also be referred to as a "deployed" position, the reamer is in a reaming position suitable for cutting bone.

With initial reference now to FIGS. 1-5, a reamer constructed in accordance with one example of the present teachings is shown and generally identified at reference numeral 10. The reamer 10 is shown in use on a glenohumeral joint 12 during shoulder arthroplasty. Prior to discussing the particular components of the reamer 10, a brief description of the glenohumeral joint 12 will be described. The glenohumeral joint 12 is generally formed between a humerus 14 and a scapula 16. Specifically, a humeral head 20 formed on the humerus 14 fits into a glenoid 22 on the end of the scapula 16.

As will become appreciated from the following discussion, a surgeon may prepare an incision 26 that is relatively small to accommodate the reamer 10 in a collapsed position (FIGS. 1 and 3). The reamer 10 may subsequently be moved to an expanded position (FIGS. 2 and 4) once inserted through the incision 26 to ream the glenoid 22. Subsequent to reaming, the reamer 10 can be returned to the collapsed position for being removed from the patient through the incision 26. The reamer 10 can generally include a first member 30 and a second member 32. The first and second members 30 and 32 can move relative to each other between the collapsed position (FIG. 3) and the expanded position (FIG. 4).

The first member 30 generally includes a first elongated hub 36 that extends along a first axis 38. The first member 30 can further include a first pair of elongated cutting arms 40 that are fixed to the first elongated hub 36 and extend along a second axis 42. In the example provided, the first and second axes 38 and 42 can be generally perpendicular relative to each other. The first elongated hub 36 defines a cannulation 44. A relief 46 can be defined in the first elongated hub 36 at a location generally adjacent to the first pair of cutting arms 40. The first pair of cutting arms 40 can include a plurality of cutting teeth 48 extending therefrom. The first member 30 can further define a track 50 formed on the first elongated hub 36. The track 50 can collectively include a first track portion 52, a second track portion 54, and a third track portion 56. A first hook 60 can be provided at a transition between the first track portion 52 and the third track portion 56. Similarly, a second hook 62 can be provided at a transition between the second track portion 54 and the third track portion 56.

The second member 32 can generally include a second elongated hub 66 that extends along a third axis 68. The second member 32 can further include a second pair of cutting arms 70 that extend along a fourth axis 72. The second elongated hub 66 of the second member 32 can include a track follower 78 extending therefrom. The second elongated hub 66 can define a cannulation 80. The cannulation 80 can accept a drill or guide pin 81 during initial alignment of the reamer 10 with the glenoid 22. The second pair of cutting arms 70 can define a plurality of teeth 82 extending therefrom. The second elongated hub 66 can be generally received by the first elongated hub 36 in an assembled position (FIGS. 3 and 4). The track follower 78 can be configured to generally ride along the track 50 to move the reamer 10 between the collapsed position (FIG. 3) to the expanded position (FIG. 4).

With particular reference now to FIGS. 3 and 4, movement of the second pair of cutting arms 70 from the collapsed position (FIG. 3) to the expanded position (FIG. 4) will be described. Notably, in the collapsed position (FIG. 3), the first and second pairs of cutting arms 40 and 70 occupy a position when the axes 42 and 72 are parallel. When moved to the expanded position (FIG. 4), the first and second pairs of cutting arms 40 and 70 occupy a position where the axes 42 and 72 are non-parallel. Initially, the track follower 78 is caused to be moved around the second hook 62 on the track 50 such as by rotating the first and second elongated hubs 36 and 66 relative to each other. In the particular configuration provided, the first elongated hub 36 is translated initially along the first axis 38 (in a direction generally leftward as viewed in FIG. 4) to move the track follower 78 around the second hook 62. The first elongated hub 36 can then be rotated around the first axis 38 in a direction indicated by arrow 80 (FIG. 4). Next, the track follower 78 can be advanced along the third track portion 56. In this regard, the first elongated hub 36 can be translated along the first axis 38 in a direction leftward as viewed in the FIG. 4.

The first and second elongated hubs 36 and 66 can then be further rotated relative to each other such that the track follower 78 locates along the first track portion 52 to a location generally around the first hook 60 (FIG. 4) in the expanded position, Again, in the configuration provided, the first elongated hub 36 is rotated around the first axis 38 in the direction indicated by arrow 80. The first elongated hub 36 can then be translated along the first axis 38 (in a direction rightward as viewed in FIG. 4) to further nest the track follower 78 around the first hook 60. Notably, the second pair of cutting arms 70 are caused to generally locate into the relief 46 on the first elongated hub 36. In the collapsed position, the sequence is reversed for moving the second pair of cutting arms 70 from the expanded position to the collapsed position.

Turning now to FIGS. 6-10, another reamer 110 constructed in accordance to additional features of the present disclosure will be described. The reamer 110 can be movable between a collapsed position (FIGS. 6 and 9) and an expanded position (FIGS. 7 and 10). As with the reamer 10 described above, the reamer 110 can be advanced through a relatively small incision, such as the incision 26 shown in FIG. 1, in the collapsed position and then subsequently moved to the expanded position to ream the glenoid 22. The reamer 110 can generally include a first member 130 and a second member 132. The first and second members 130 and 132 can move relative to each other between the collapsed position (FIG. 6) and the expanded position (FIG. 7).

The first member 130 generally includes a first elongated hub 136 that extends along a first axis 138. The first member 130 can further include a first pair of elongated cutting arms 140 that are fixed to the first elongated hub 136 and extend along a second axis 142. The second axis 142 is generally defined along a center of gravity of the first pair of elongated cutting arms 140 that intersects the first axis 138. In the example provided, the first and second axes 138 and 142 can be generally perpendicular relative to each other. The first elongated hub 136 defines a cannulation 144. The first pair of cutting arms 140 can include a plurality of cutting teeth 148 extending therefrom. The first member 130 can further define a track 150 formed on the first elongated hub 136.

The second member 132 can generally include a second elongated hub 166 that extends along a third axis 168. The second member 132 can further include a second pair of cutting arms 170 that extend along a fourth axis 172. The fourth axis 172 is generally defined along a center of gravity of the second pair of cutting arms 170 that intersects the third axis 168. The second hub 166 of the second member 132 can include a track follower 178 extending therefrom. In the example shown, the track follower 178 can be fixedly secured into an aperture 179 defined in the second elongated hub 166. The second pair of cutting arms 170 can include a plurality of teeth 182 extending therefrom. The second elongated hub 166 can be generally received by the first elongated hub 136 in an assembled position (FIGS. 6 and 7). The track follower 178 can be configured to generally ride along the track 150 to move the reamer 10 between the collapsed position (FIG. 6) to the expanded position (FIG. 7).

With particular reference now to FIGS. 6, 7, 9 and 10, movement of the second pair of cutting arms 180 from the collapsed position (FIGS. 6 and 9) to the expanded position (FIGS. 7 and 10) will be described. In one example, the reamer 110 can be normally positioned in the collapsed position (FIGS. 6 and 9) when at rest. In some examples, a biasing member (not specifically shown) may be configured to urge the respective first and second pair of cutting arms 140 and 170 into the collapsed position. When the reamer 110 is caused to rotate in a direction generally indicated by arrow 183 (FIG. 7), such as when coupled to and driven by a driver, the second pair of cutting arms 170 are caused to move into the expanded position (FIG. 7) as the track follower 178 rides along the track 150 from the location shown in FIG. 6 to the location shown in FIG. 7. When a surgeon has determined that the glenoid 22 has been reamed sufficiently, the driver of the reamer 110 is stopped and the first and second pairs of arms 140 and 170 are caused to return to the collapsed position in FIG. 6 and reamer 110 is removed through the incision (such as the incision 26 shown in FIG. 1).

With particular reference now to FIGS. 11 and 12, another reamer 110' constructed in accordance to additional features of the present teachings will be described. The reamer 110' is generally constructed similar to the reamer 110 described above in detail. In this regard, reference numerals having a prime suffix will be used to denote similar components from the reamer 110. The reamer 110' is configured to be moved from a collapsed position (FIG. 12) to an expanded position (FIG. 11). In this regard, a surgeon may insert the reamer 110' through a small incision 26 and subsequently move the reamer 110' to the expanded position upon coupling of a driving force onto the reamer 110'. The reamer 110' can generally include a first member 130' and a second member 132'. The first and second members 130' and 132' can move relative to each other between the collapsed position (FIG. 12) and the expanded position (FIG. 11). The first member 130' can generally include a first elongated hub 136' that extends along a first axis 138'. The first member 130' can further include a first pair of elongated cutting arms 140' that are fixed to the first elongated hub 136' and extend along a second axis 142'. The first pair of cutting arms 140' can include a plurality of cutting teeth 148' extending therefrom. The first member 130' can further define a track 150' formed on the first hub 136'.

The second member 132' can generally include a second elongated hub 166' that extends along a third axis 168'. The second member 132' can further include a second pair of cutting arms 170' that extend along a fourth axis 172'. A biasing member 173 can be coupled between the first and second elongated hubs 136' and 166' for biasing the first and second members 130' and 132' toward the collapsed position (FIG. 12). During rotation of the reamer 110' by a driver during a reaming event, the bias of the spring 173 is overcome causing the second pair of cutting arms 170' to rotate in the direction of arrow 175 (FIG. 11). When a rotational driving force is stopped, the biasing member 173 urges the second pair of cutting arms 170' back to the collapsed position as shown in FIG. 12 whereby a surgeon may withdraw the reamer through the incision 26.

Turning now to FIGS. 13-15, another reamer constructed in accordance to additional features of the present disclosure is shown and generally identified at reference numeral 210. The reamer 210 can generally incorporate three distinct cutting tools in a single component. In this regard, the reamer 210 includes an elongated body 212 that extends along an axis 214. The reamer 210 collectively includes a modular post cutting portion 220, a boss cutting portion 222, and a glenoid face reamer portion 224. In the particular example shown, the modular post cutting portion 220 can collectively include a first stepped cutting portion 230, a second stepped cutting portion 232, and a third stepped cutting portion 234. The third stepped cutting portion 234 can generally transition into the boss cutting portion 222. The glenoid face reamer portion 224 can generally include a first pair of elongated arms 240 and a second pair of elongated arms 242. The first pair of elongated arms 240 can generally extend along a first axis 244. The second pair of elongated arms 242 can generally extend along a second axis 246. The first and second axes 244 and 246 can be generally perpendicular to the axis 214.

With reference now to FIG. 16, an exemplary glenoid component that may be implanted into the prepared glenoid resulting from using the reamer 210 (FIGS. 13-15) is shown and generally identified at reference numeral 250. The glenoid component 250 generally includes a platform portion 252, a central post or stem 254, and a plurality of peripheral pegs 256. A boss 260 having a radius is generally formed at a transition between the platform portion 252 and the stem 254. As can be appreciated, the boss 260 can be configured to be implanted into a reamed space formed from the boss cutting portion 222 of the reamer 210. Similarly, the stem 254 can have a series of stepped segments that can have a geometry that corresponds to the opening formed with the stepped portions 230, 232 and 234 of the modular post cutting portion 220. As can be appreciated, the reamer 210 having the three cutting portions (modular post cutting portion 220, boss cutting portion 222, and glenoid face reamer portion 224) formed as a single component can allow the surgeon to prepare an opening in the glenoid 22 with a single cutting step suitable for receipt of the glenoid component 250.

Figure 19:
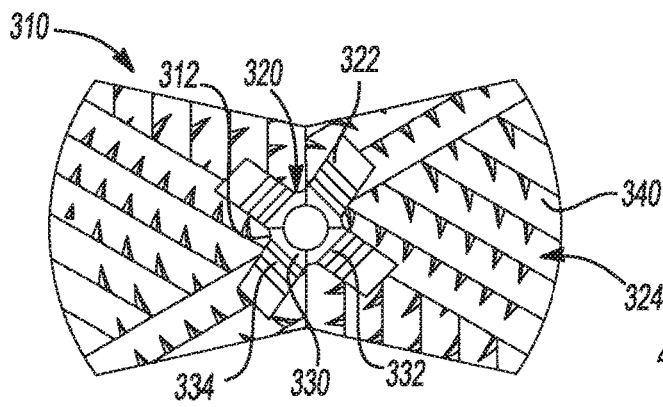
FIG. 19 is a bottom plan view of the reamer of FIG. 17.

Turning now to FIGS. 17-19, another reamer constructed in accordance to additional features of the present disclosure is shown and generally identified at reference numeral 310, The reamer 310 can generally incorporate three distinct cutting tools in a single component. In this regard, the reamer 310 includes an elongated body 312 that extends along an axis 314. The reamer 310 collectively includes a modular post cutting portion 320, a boss cutting portion 322, and a glenoid face reamer portion 324. In the particular example shown, the modular post cutting portion 320 can collectively include a first stepped cutting portion 330, a second stepped cutting portion 332, and a third stepped cutting portion 334. The third stepped cutting portion 334 can generally transition into the boss cutting portion 322. The glenoid face reamer portion 324 can include a plurality of cutting teeth 340 formed thereon. As with the reamer 210 described above, the reamer 310 having the three cutting portions (modular post cutting portion 320, boss cutting portion 322, and glenoid face reamer portion 324) formed as a single component can allow a surgeon to prepare an opening in the glenoid 22 with a single cutting step suitable for receipt of a glenoid component such as the glenoid component 250 illustrated in FIG. 16.

Figure 20:
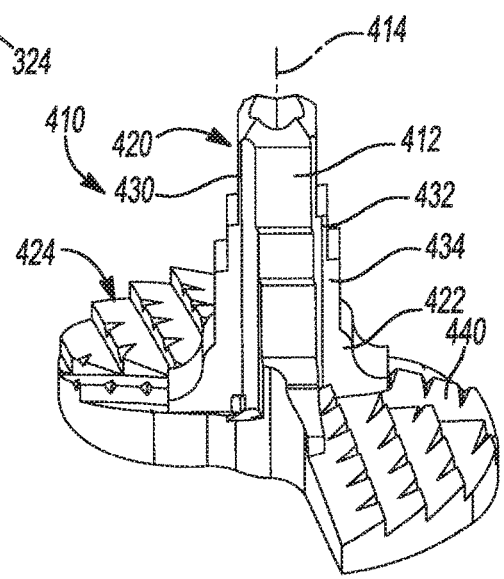
FIG. 20 is a bottom perspective view of a glenoid reamer constructed in accordance to still another configuration of the present disclosure.
Figure 21:
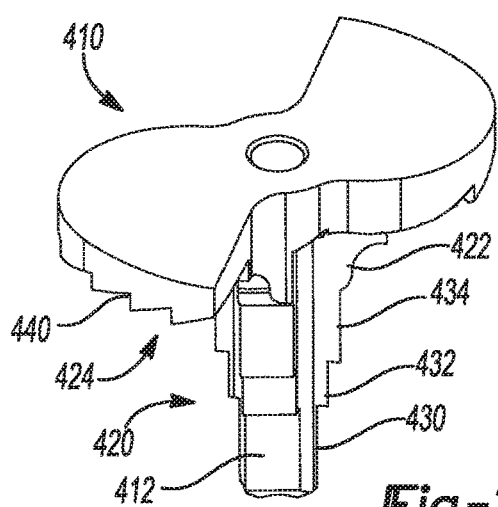
FIG. 21 is a top perspective view of the glenoid reamer of FIG. 20.
Figure 22:
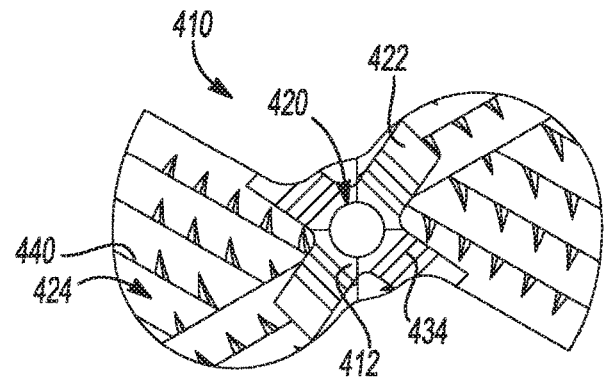
FIG. 22 is a bottom plan view of the glenoid reamer of FIG. 20.

Turning now to FIGS. 20-22, another reamer constructed in accordance to additional features of the present disclosure is shown and generally identified at reference numeral 410. The reamer 410 can generally incorporate three distinct cutting tools in a single component. In this regard, the reamer 410 includes an elongated body 412 that extends along an axis 414. The reamer 410 collectively includes a modular post cutting portion 420, a boss cutting portion 422, and a glenoid face reamer portion 424. In the particular example shown, the modular post cutting portion 420 can collectively include a first stepped cutting portion 430, a second stepped cutting portion 432, and a third stepped cutting portion 434. The third stepped cutting portion 434 can generally transition into the boss cutting portion 422. The glenoid face reamer portion 424 can generally include a plurality of teeth 440 formed thereon. As best illustrated in the plan view of FIG. 22, the reamer 410 can generally provide a profile similar to a blade or propeller that has a reduced overall profile that can be suitable for insertion through the incision 26 (FIG. 1). The profile of the reamer 410 can also provide minimal impact such that it may glance off of obstructions providing a "soft" interference such as during insertion through the incision 26.

Figure 23:
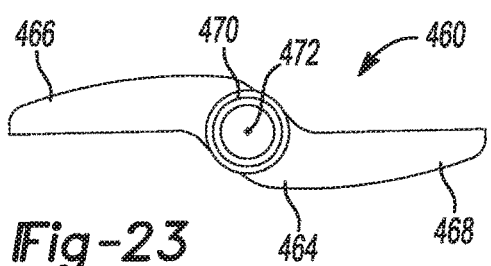
FIG. 23 is a bottom plan view of a glenoid reamer constructed in accordance to still another configuration of the present disclosure.
Figure 24:
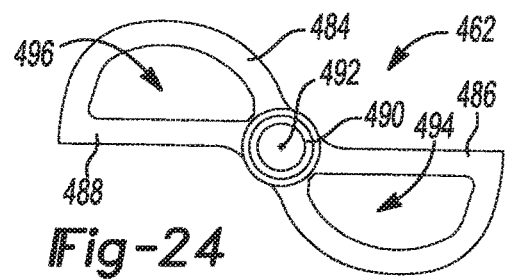
FIG. 24 is a bottom plan view of another glenoid reamer constructed in accordance to another configuration of the present disclosure.

Turning now to FIGS. 23 and 24, additional reamers constructed in accordance to the present teachings are shown and generally identified at reference numerals 460 and 462, respectively. The reamer 460 generally includes a body portion 464 having a first blade portion 466 and a second blade portion 468. The body 464 can generally include a central hub 470 that has an axis 472 around which the reamer 460 is configured to rotate. Notably, the profile of the reamer 460 is relatively reduced such that it may be easily inserted through a small incision such as the incision 26 illustrated in FIG. 1. The reamer 462 generally includes a body 484 having a first blade portion 486 and a second blade portion 488. The body 484 can further include a hub 490 that rotates around an axis 492. The blades 486 and 488 can generally define an opening 494 and 496, respectively. As with the reamer 460 illustrated in FIG. 23, the reamer 462 can have a generally reduced profile that can be suitable for insertion through an incision such as the incision 26 shown in FIG. 1. Additionally, the openings 494 and 496 can allow the surgeon additional viewing (e through the openings 494 and 496) of the reaming site such as during initial positioning of the reamer 462 relative to the glenoid 22.

Figure 30:
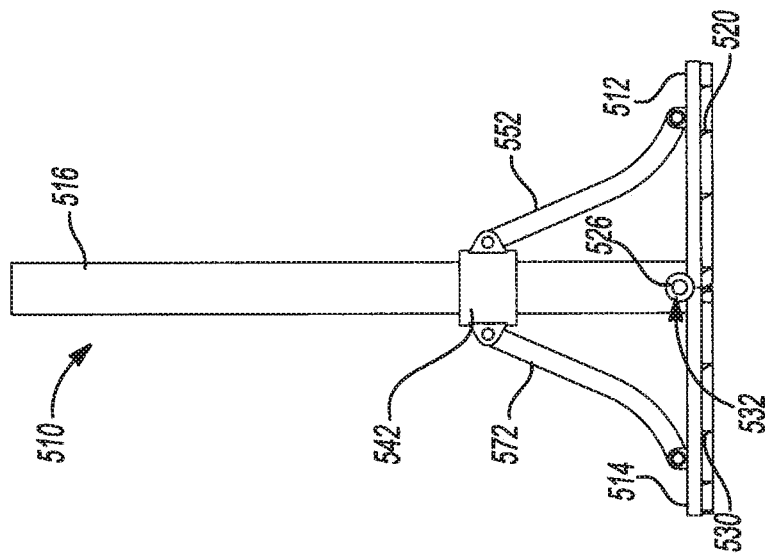
FIGS. 28-30 is an exemplary sequence of moving the glenoid reamer of FIG. 25 from the collapsed position (FIG. 28) to the expanded position (FIG. 30)

With reference now to FIGS. 25-30, another reamer constructed in accordance to additional features of the present teachings is shown and generally identified at reference numeral 510. The reamer 510 generally includes a first and a second cutting portion 512 and 514, respectively that move relative to a shaft 516 between a collapsed position (FIG. 28) to an expanded position (FIG. 30). The first cutting portion 512 can generally include a semi-circular profile having first hinge portions 516 and a first cutting portion mounting ear 518 formed thereon. The first cutting portion 512 can further include a plurality of teeth 520 formed thereon. The second cutting portion 514 can be similarly constructed to the first cutting portion 512. In this regard, the second cutting portion 514 can generally include a semi-circular profile having second hinge portions 526 and a second cutting portion mounting ear 528 formed thereon. A plurality of cutting teeth 530 can be formed on the second cutting portion 514. The shaft 516 can further include a hinge arm 532 that extends generally transverse to the shaft 516. The hinge arm 532 can be cannulated and configured to receive a hinge pin 540 therethrough. A collar 542 can be journaled around the shaft 516 and configured for translation along the shaft 516. The collar 542 can include collar mounting ears 550 and 551. A first arm 552 can be connected between the first cutting portion 512 and the collar 542. More specifically, an axle 554 can be located through an aperture 556 formed in a first end of the arm 552 and a complementary aperture 558 in the first cutting portion mounting ear 518. A pin 560 can be configured to locate through an aperture 562 formed in an opposite end of the arm 552. The pin 560 can further locate through an aperture 564 defined through the collar mounting ear 550. A second arm 572 can be coupled to the second cutting portion 514 by way of an axle 574 that locates through an aperture 576 in the second cutting portion mounting ear 528 and a complementary aperture 578 formed in the second arm 572. An opposite end of the arm 572 can have an aperture 580 configured to receive a pin 582 that also locates through apertures 584 in the collar mounting ear 551.

Figure 29:
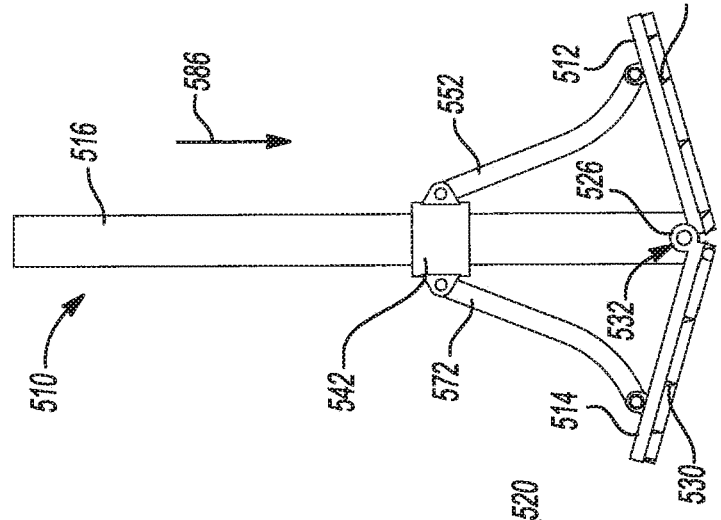
Figure 28:
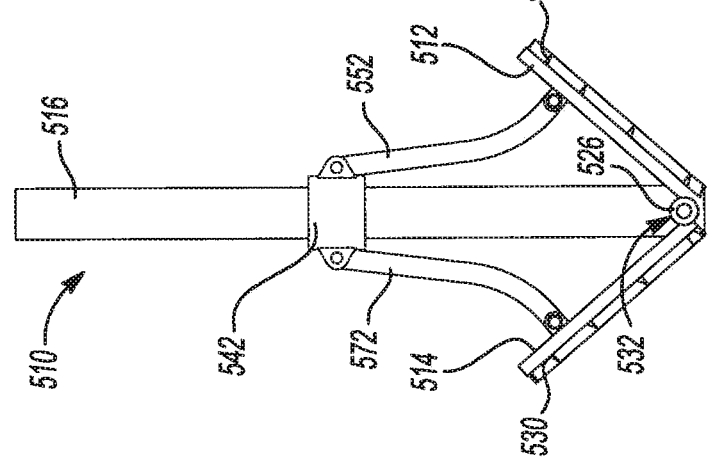

With continued reference to FIGS. 25-27 and particular reference to FIGS. 28-30, an exemplary sequence for moving the reamer from the collapsed position (FIG. 28) to the expanded position (FIG. 30) will be described. At the outset, a surgeon may insert the first and second cutting portions 512 and 514 through an incision such as the incision 26 shown in FIG. 1, Next, a surgeon may advance the collar 542 in the direction identified by arrow 586 in FIG. 29. Translation of the collar 542 in the direction of arrow 586 can cause the arms 552 and 572 to urge the first and second cutting portions 512 and 514, respectively around the hinge pin 540 until reaching the position shown in FIG. 30. It will be appreciated that the first and second arms 552 and 572 are caused to concurrently rotate around the pins 560 and 582 coupled to the collar 542. Similarly, the arms 552 and 572 are caused to rotate around the axles 554 and 574 mounted on the first and second mounting ears 518 and 528, respectively. Once a surgeon has sufficiently reamed the glenoid 22 with the reamer 510, the surgeon can translate the collar 542 in a direction opposite the arrow 586 to return the first and second cutting portions 512 and 514, respectively to the collapsed position for removal out through the incision 26.

Figure 31:
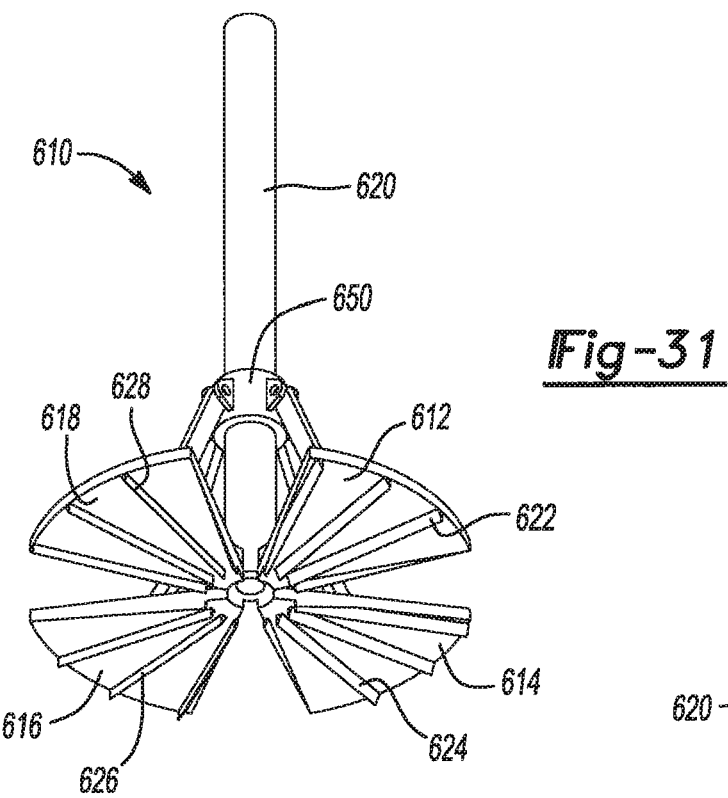
FIG. 31 is a bottom perspective view of another glenoid reamer constructed in accordance to the present disclosure and shown in an expanded position.
Figure 32:
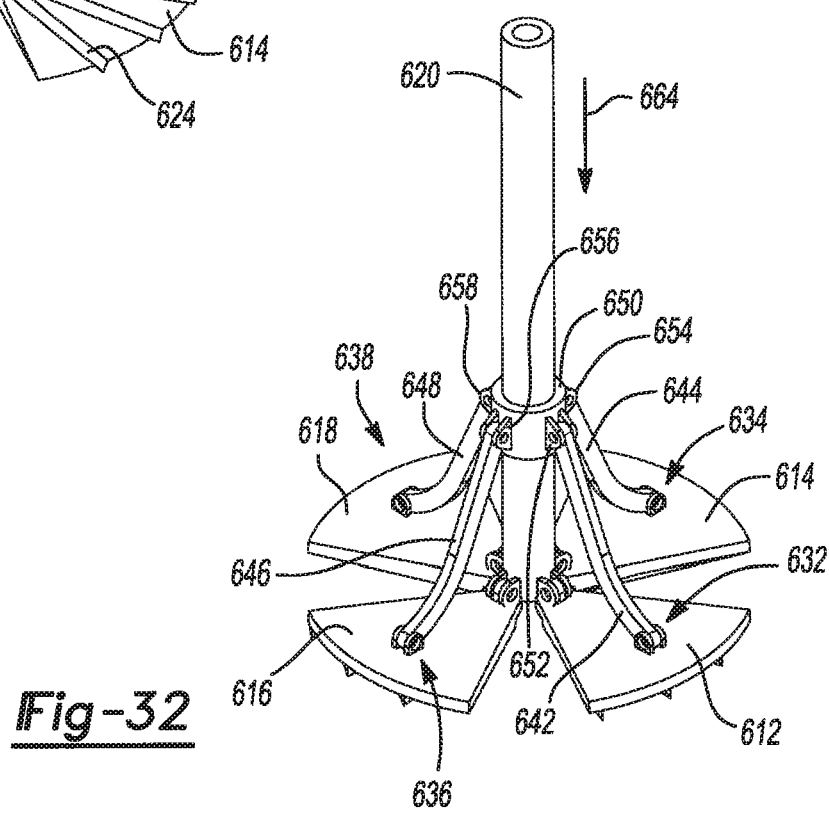
FIG. 32 is a top perspective view of the glenoid reamer of FIG. 31.

With reference now to FIGS. 31 and 32, another reamer constructed in accordance to additional features of the present teachings is shown and generally identified at reference numeral 610. The reamer 610 generally includes a first, a second, a third, and a fourth cutting portion 612, 614, 616, and 618, respectively. The first, second, third, and fourth cutting portions 612, 614, 616, and 618 are configured to move relative to a shaft 620 between a collapsed position (not specifically shown but similar to the profile identified in FIG. 28) to an expanded position (FIGS. 31 and 32). Each of the first, second, third, and fourth cutting portions 612, 614, 616, and 618 can include a partial quarter-circular profile. The first cutting portion 612 can include a plurality of teeth 622 formed thereon. The second cutting portion 614 can include a plurality of cutting teeth 624 formed thereon. The third cutting portion 616 can include a plurality of cutting teeth 626 formed thereon. The fourth cutting portion 618 can include a plurality of cutting teeth 628 formed thereon. The first cutting portion 612 can have a hinge portion 632 formed thereon. The second cutting portion 614 can have a second hinge 634 formed thereon. The third cutting portion 616 can include a third hinge 636 formed thereon. The fourth cutting portion 618 can have a fourth hinge 638 formed thereon.

A first, second, third, and fourth arm 642, 644, 646, and 648 can be mounted between the first, second, third, and fourth cutting portions 612, 614, 616, 618, and a collar 650. Specifically, the collar 650 can have a first hinge portion 652, a second hinge portion 654, a third hinge portion 656, and a fourth hinge portion 658 that couples with the respective arms 642, 644, 646, and 648. Translation of the collar 650 in the direction identified by arrow 664 causes the first, second, third, and fourth cutting portions 612, 614, 616, and 618 to be moved to the expanded position shown in FIG. 32. Movement of the collar 650 from the position shown in FIG. 32 in a direction opposite the arrow 664 causes the first, second, third, and fourth cutting portions 612, 614, 616, and 618 to return back to the collapsed position (again, similar to shown in FIG. 28).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present, Other words used to describe the relationship between elements should be interpreted in a like fashion (e.g., "between" versus "directly between," "adjacent" versus "directly adjacent," etc.), As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A bone reamer comprising:
   a hub having a central axis;
   a body having a first body portion extending from the hub and a second body portion extending in an opposite direction from the hub;
   a first blade extending entirely straight from the hub to a distal end of the first body portion; and
   a second blade extending entirely straight from the hub to a distal end of the second body portion, the second blade arranged in a plane with the first blade,
   wherein the first body portion and the first blade form a first opening that is perpendicular to an axis of rotation,
   wherein the second body portion and the second blade form a second opening that is perpendicular to an axis of rotation.

2. The bone reamer of claim 1, wherein a cutting surface of the first blade and a cutting surface of the second blade are substantially co-planar.

3. The bone reamer of claim 1, wherein the first body portion and the second body portion are curved.

4. The bone reamer of claim 1, wherein the first opening and the second opening are substantially similar.

5. The bone reamer of claim 1, wherein the first body portion, the second body portion, the first blade, and the second blade define a propeller-shaped profile.

6. A bone reamer comprising:
   a central hub having a central axis;
   a first blade extending entirely straight from the central hub and including a first cutting surface; and
   a second blade extending entirely straight from the central hub and arranged in a same plane as the first blade, the second blade including a second cutting surface, the first cutting surface and the second cutting surface arranged in a plane that passes through the central axis.

7. The bone reamer of claim 6, further comprising a body having a first body portion extending from the hub and a second body portion extending in an opposite direction from the hub, the first body portion and the second body portion being curved.

8. The bone reamer of claim 6, wherein the first blade and the second blade are solid.

9. The bone reamer of claim 6, wherein the first blade and the second blade define a propeller-shaped profile.

10. A bone reamer comprising:
    an elongated body that extends along a central axis;
    a modular post cutting portion extending from the elongated body along the central axis; and
    a glenoid face reamer portion comprising:
      a first blade portion extending from the elongated body perpendicular to the central axis, the first blade portion including a first planar cutting surface disposed along a first leading edge of the first blade portion and a first curved surface disposed along a first trailing edge of the first blade portion,
      a second blade portion extending from the elongated body perpendicular to the central axis, the second blade portion including a second planar cutting surface disposed along a second leading edge of the second blade portion and a second curved surface disposed along a second trailing edge of the second blade portion, and
      a plurality of teeth extending from the glenoid face reamer portion normal to the first and second planar cutting surfaces, wherein a first subset of the plurality of teeth are arranged parallel to the first planar cutting surface and a second subset of the plurality of teeth are arranged at an obtuse angle relative to the first subset of the plurality of teeth.

11. The bone reamer of claim 10, further comprising a boss cutting portion extending from the glenoid face reamer along the central axis.

12. The bone reamer of claim 10, wherein the modular post cutting portion includes a first stepped cutting portion, a second stepped cutting portion, and a third stepped cutting portion.

13. The bone reamer of claim 12, further comprising a boss cutting portion, the third stepped cutting portion transitioning into the boss cutting portion.

14. The bone reamer of claim 10, wherein the first planar cutting surface of the first blade portion and the second planar cutting surface of the second blade portion are substantially co-planar.

15. The bone reamer of claim 10, wherein the glenoid face reamer portion defines a propeller-shaped. profile.

16. The bone reamer of claim 10, wherein the elongated body defines a through hole along the central axis.

* * * * *